US010336965B2

(12) United States Patent
Massetti et al.

(10) Patent No.: US 10,336,965 B2
(45) Date of Patent: Jul. 2, 2019

(54) PROCESS FOR THE EXTRACTION OF LIPIDS AND SUGARS FROM ALGAL BIOMASS

(71) Applicant: ENI S.p.A., Rome (IT)

(72) Inventors: Felicia Massetti, Casteinuovo di Porto (IT); Federico Capuano, Rieti (IT); Roberto Medici, Rome (IT); Roberta Miglio, Oleggio (IT)

(73) Assignee: ENI S.p.A., Rome (IT)

( * ) Notice: Subject to any disclaimer, the term of this patent is extended or adjusted under 35 U.S.C. 154(b) by 0 days.

(21) Appl. No.: 15/037,225

(22) PCT Filed: Nov. 18, 2014

(86) PCT No.: PCT/IB2014/066130
§ 371 (c)(1),
(2) Date: May 17, 2016

(87) PCT Pub. No.: WO2015/075630
PCT Pub. Date: May 28, 2015

(65) Prior Publication Data
US 2016/0289592 A1    Oct. 6, 2016

(30) Foreign Application Priority Data
Nov. 19, 2013    (IT) .............................. MI2013A1915

(51) Int. Cl.
*C11B 1/10*    (2006.01)
*C13K 1/00*    (2006.01)
(Continued)

(52) U.S. Cl.
CPC ................. *C11B 1/10* (2013.01); *C12N 1/02* (2013.01); *C12N 1/12* (2013.01); *C13K 1/00* (2013.01);
(Continued)

(58) Field of Classification Search
CPC ................................... C12N 1/12; C11B 1/10
See application file for complete search history.

(56) References Cited

U.S. PATENT DOCUMENTS 4,328,118 A * 5/1982 Friedmann .............. C05F 11/00
516/77
2008/0160593 A1* 7/2008 Oyler ....................... C10G 3/00
435/166
(Continued)

FOREIGN PATENT DOCUMENTS

WO    WO 2009/077087 A1    6/2009
WO    WO 2014/092993    *    6/2014

OTHER PUBLICATIONS

High Lagoon pH caused by Algae Tyler Kerns Aquafix, pp. 1-5, Apr. 20, 2015.*
(Continued)

*Primary Examiner* — Douglas B Call
(74) *Attorney, Agent, or Firm* — Oblon, McClelland, Maier & Neustadt, L.L.P.

(57) ABSTRACT

Process for the extraction of lipids and sugars from algal biomass, which comprises: —producing an aqueous suspension of algal biomass; —bringing the pH of said aqueous suspension of algal biomass to a value higher than or equal to 10, preferably ranging from 10.2 to 12, obtaining an aqueous suspension of algal biomass at basic pH; —adding at least one anionic flocculant to said aqueous suspension of algal biomass at basic pH obtaining a concentrated algal biomass; —recovering said concentrated algal biomass; —subjecting said concentrated algal biomass to extraction of the lipids obtaining: (i) an organic phase comprising lipids; (ii) a semi-solid phase comprising a residue of said algal biomass; —subjecting said semi-solid phase (ii) to hydrolysis obtaining sugars. The lipids thus obtained can be advantageously used in the production of biodiesel or green
(Continued)

diesel which can be used as such, or in a mixture with other fuels for motor vehicles. The sugars thus obtained can be advantageously used as carbon sources in fermentation processes for the production of lipids and also for the production of alcohols (e.g., ethanol, butanol). Said alcohols can be advantageously used as biofuels for motor vehicles or as components that can be added to fuels for motor vehicles.

20 Claims, 3 Drawing Sheets

(51) Int. Cl.
    *C13K 13/00*     (2006.01)
    *C12N 1/02*     (2006.01)
    *C12N 1/12*     (2006.01)

(52) U.S. Cl.
    CPC .......... *C13K 13/002* (2013.01); *C13K 13/007* (2013.01); *Y02E 50/13* (2013.01)

(56) References Cited

U.S. PATENT DOCUMENTS

| | | | |
|---|---|---|---|
| 2010/0124774 A1* | 5/2010 | Kim | C12P 7/04 435/150 |
| 2011/0020913 A1 | 1/2011 | Rispoli et al. | |
| 2011/0201076 A1* | 8/2011 | Liang | C07K 14/71 435/173.9 |
| 2012/0022278 A1 | 1/2012 | Aravanis et al. | |
| 2012/0253056 A1 | 10/2012 | Cranford et al. | |
| 2013/0274490 A1* | 10/2013 | Hippler | C11L 31/10 554/19 |
| 2015/0284673 A1* | 10/2015 | Langer | C12N 1/12 435/257.5 |

OTHER PUBLICATIONS

Production and harvesting of microalgae for wastewater treatment, biofuels, and bioproducts. Logan Christenson et al. Biotechnology Advances, vol. 29, pp. 686-702 (Year: 2011).*

International Search Report dated Apr. 20, 2015 in PCT/162014/066130.

Lucelia Borges, et al., "Effects of flocculants on lipid extraction and fatty acid composition of the microalgae *Nannochloropsis oculata* and *Thalassiosira weissflogil*" Biomass and Bioenergy, vol. 35, XP028308684, 2011, pp. 4449-4454.

Angel D. Gonzalez-Delgado, et al., "Energy Integration of Bioethanol Production Process Topology from Microalgae Biomass: Evaluation of SSCF, SSF, Acid Hydrolysis and Product Purification Alternatives" Chemical Engineering Transactions, vol. 35, XP002723191, 2013, pp. 1069-1074.

\* cited by examiner

Pond P-1

PROCESS FOR THE EXTRACTION OF LIPIDS AND SUGARS FROM ALGAL BIOMASS

The present invention relates to a process for the extraction of lipids and sugars from algal biomass.

More specifically, the present invention relates to a process for the extraction of lipids and sugars from algal biomass which comprises producing an aqueous suspension of algal biomass; bringing the pH of said algal biomass to a value higher than or equal to 10; concentrating said aqueous suspension of algal biomass by the addition of at least one anionic flocculant; recovering the concentrated algal biomass obtained; subjecting said concentrated algal biomass to lipid extraction, obtaining: (i) an organic phase comprising lipids; (ii) a semi-solid phase comprising a residue of said algal biomass; subjecting said semi-solid phase (ii) to hydrolysis obtaining sugars.

Figure 1:
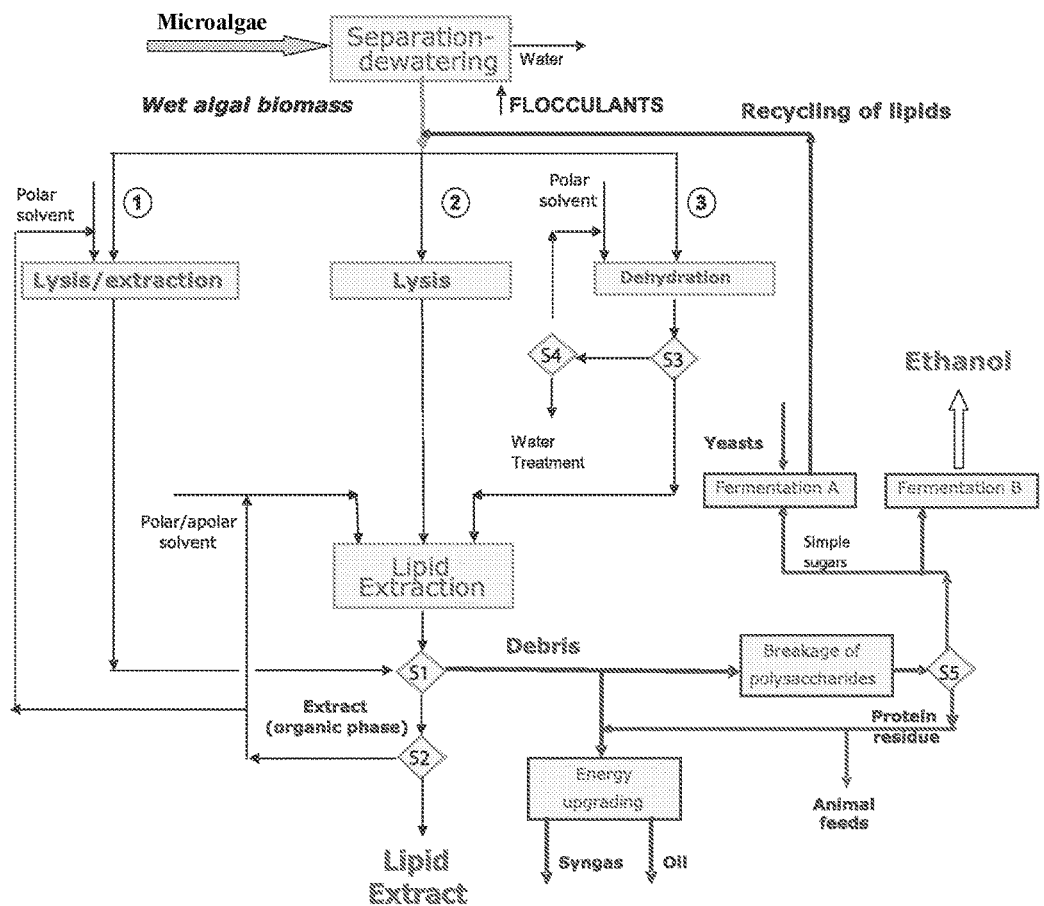
FIG. 1 shows various embodiments of the present invention.

The sugars thus obtained can be advantageously used as carbon sources in fermentation processes for the production of lipids and also for the production of alcohols (e.g., ethanol, butanol). Said alcohols can be advantageously used as biofuels for motor vehicles, or as components that can be added to fuels for motor vehicles.

Algae, in particular microalgae, are currently cultivated for the production of valuable compounds such as, for example, poly-unsaturated fatty acids [for example, eicosapentaenoic acid (EPA), docosahexaenoic acid (DHA), and similar products], vitamins (for example, β-carotene, and similar products) and gelling agents, which are included in the nutritional, pharmaceutical and cosmetic fields.

The cultivation of microalgae for the above sectors is characterized by rather limited production capacities (in the order of hundreds-thousands of tons per year) and by the high added value of the compounds obtained (hundreds-thousands of dollars per kilogram). This is why complex and expensive production systems, particularly extraction and purification systems, which must satisfy strict regulations of the sanitary and nutritional type, typical of the above-mentioned fields, can be tolerated.

The shift from the above-mentioned fields of the traditional use of microalgae, to the environmental/energy field, requires the development of technologies which lead to considerable increases in the production capacity (from hundreds-thousands of tons per year to millions of tons per year) and to a large reduction in the production costs due to the limited added value of the compounds destined for the environmental/energy field (hundreds-thousands of dollars per ton).

Processes relating to the extraction of compounds from algal biomasses are described in the art.

International patent application WO 2010/000416, in the name of the Applicant, for example, describes a process for the extraction of fatty acids from algal biomass which comprises: producing an aqueous suspension of algal biomass; subjecting the aqueous suspension of algal biomass to acid hydrolysis and extraction by the addition of at least one apolar organic solvent and of at least one inorganic acid to said aqueous suspension of algal biomass, thus obtaining the following three phases: (i) a semi-solid phase comprising a muddy residue of algal biomass; (ii) an aqueous phase comprising inorganic compounds and hydrophilic organic compounds; (iii) an organic phase comprising fatty acids and hydrophobic organic compounds different from said fatty acids. Said phases (i)-(iii) are subjected to further treatments in order to obtain: pyrolytic oils, biodiesel or green diesel, biogas.

International patent application WO 2010/089063, in the name of the Applicant, describes a process for the extraction of lipids from algal biomass which comprises: producing an aqueous suspension of algal biomass; adding, to said aqueous suspension of algal biomass, at least one organic solvent immiscible or substantially immiscible with water obtaining an aqueous-organic mixture; subjecting said aqueous-organic mixture to evaporation of the water and extraction of the lipids; operating at such a temperature so as to obtain the substantial complete removal of the water from said aqueous-organic mixture obtaining: (i) an organic phase comprising lipids and said organic solvent; (ii) a semi-solid phase comprising a residue of said algal biomass. Said phases (i) and (ii) being subjected to further treatments in order to obtain: pyrolytic oils, biodiesel or green diesel, biogas.

American patent application US 2011/0086386 describes a fractionation method of biomass (for example, algal biomass) which comprises the following steps: conditioning the permeability of a biomass suspended in an aqueous solution of at least one solvent, bringing it to a certain pH (for example, a pH ranging from 1 to 6.5 or a pH ranging from 7.5 to 14), so as to form a conditioned biomass; putting the conditioned biomass in close contact with at least one apolar solvent; separating in order to obtain a solution of apolar solvent and a polar solution of biomass; recovering the cell products from the solution of apolar solvent and the polar solution of biomass; subjecting the polar solution of biomass to fractionation in order to obtain polar components and components soluble in water. Said method allows not only the products of interest (which can in their turn be used in the nutritional or pharmaceutical field, or in the biofuels field), but also the by-products, to be recovered and the recycling of nutrients and water.

American U.S. Pat. No. 7,869,195, describes a method for extracting lipids and for dehydrating a wet biomass which comprises: centrifuging a wet algal biomass in order to increase the solid content from about 10% to about 40%, obtaining a centrifuged algal biomass; mixing the centrifuged algal biomass with an amphiphilic solvent obtaining a mixture; heating the mixture, obtaining a dehydrated and defatted algal biomass; separating the amphiphilic solvent from the dehydrated and defatted algal biomass, obtaining amphiphilic solvent, water and lipids; evaporating the amphiphilic solvent from the water and lipids; and separating the water from the lipids. Said lipids can be used for producing biofuels and renewable energy.

American U.S. Pat. No. 8,115,022, describes a method for isolating chlorophylls and oil rich in omega-3 from algae which comprises: (a) dehydrating substantially intact algal cells suspended in a liquid medium, obtaining an algal biomass; (b) extracting (for example, by the addition of ethanol) a substantially liquid fraction comprising neutral lipids, carotenoids, and chlorophylls from the algal biomass, said neutral lipids comprising omega-3 fatty acids; and (c) separating the carotenoids and chlorophylls from the neutral lipids (for example, by means of an adsorbing material or of a diafiltration membrane). Said lipids can be used for producing biofuels.

It is also known that the collection of algal biomass is relatively complicated and costly (it can in fact account for 20%-30% of the total cost of the production process of algal biomass.

Studies have consequently been carried out for improving the collection process of algal biomass.

Molina Grima E. et al., in "Biotechnology Advances" (2003), Vol. 20, pages 491-515, for example, describe various processes for collecting algal biomass such as, for example, flocculation, centrifugation, filtration. With respect to flocculation, the use of flocculating agents is described, such as, for example: metal salts (e.g., iron chloride, aluminum sulfate, iron sulfate); salts of polymerized metals (e.g., polyferric sulfate); cationic polymers (polyelectrolytes); bioflocculants (e.g., chitosan). Or, said flocculation can be carried out by bringing the pH of the culture broth of the algal biomass to a value ranging from 11.8 to 12.

Knuckey R. M. et al., in "Aquacultural Engineering" (2006), Vol. 35, Issue 3, pages 300-313, describe a flocculation technique for marine microalgae which comprises bringing the pH of the culture broth of said microalgae to a value ranging from 10 to 10.6 using sodium hydroxide (NaOH), adding a non-ionic polymer (Magnafloc LT-25) at a final concentration equal to 0.5 mg/l. The flocculated product obtained is recovered and neutralized with an acid in order to obtain a concentration factor of said microalgae ranging from 200 to 800 times.

Brennan L. et al., in "Renewable and Sustainable Energy Reviews" (2010), Vol. 14, Issue 2, pages 557-577, describe the production of biofuels from microalgae. Among the various processes for the recovery of the microalgae from the culture broth, flocculation in the presence of metal salts (e.g., iron chloride, aluminum sulfate, iron sulfate); non-ionic polymers (e.g., Magnafloc LT-25); bioflocculants (e.g., chitosan), is described. Or, said flocculation can be carried out by means of ultrasounds.

American patent application US 2009/0162919 describes a method for the concentration of unicellular microalgae which comprises: a) putting microalgae having an average diameter of the single cells of less than 20 μm in contact, in an aqueous environment, with an inorganic flocculating agent (e.g. aluminium chloride, aluminium sulfate, polyaluminium chloride, sodium aluminate), present at a concentration lower than 10% with respect to the dry microalgal biomass, obtaining a solution comprising flocculated microalgae in flocs having an average diameter of at least 100 μm; and b) separating the microalgae flocs from the aqueous environment, obtaining a biomass of microalgae having a concentration of at least 1%. Flocs having an average diameter in the order of millimeters can be obtained by adding a further flocculant to said solution, selected from cationic or non-ionic organic polymers, or from biopolymers such as, for example, chitosan, clays.

The processes described above, however, can have some critical points.

Reactions that allow the flocculation of algal biomass are, in fact, sensitive to various parameters such as, for example, pH, temperature, cell surface properties of the algae used, concentration of the chemicals used for the growth of the algae, salinity of the culture medium used (in particular, in the case of algae growing in salt water), COD ("Chemical Oxygen Demand") value, contaminating species (e.g., bacteria) that can be present in the environment in which the algae grow (in particular if cultivated in open ponds), ionic force of the aqueous phase, but above all to the vegetative state (vitality) of the alga. The vegetative state of the alga, in fact, varies significantly during the day for various reasons such as, for example: as a consequence of the variation in the solar light, with the induction of photo-acclimatization and photo-inhibition phenomena; in relation to the cultivation method, batch, semi-batch or in continuous; in relation to the various growth phases of the alga, i.e. the exponential growth phase, the maturation phase, the starvation phase. The numerous variables that influence the flocculation process consequently make it impossible to predict operational conditions having a definite efficacy and make it indispensable to carry out various experimental tests which, in any case, when brought to an industrial level, may prove to not always be effective.

The Applicant has therefore considered the problem of finding a process for the extraction of lipids and sugars from algal biomass in which the flocculation process is capable of overcoming the above critical aspects, is reproducible and can be applied on an industrial scale.

The Applicant has now found a process for the extraction of lipids and sugars from algal biomass in which the flocculation of said algal biomass can be advantageously carried out by means of a shift of the pH of the aqueous suspension containing the algal biomass, obtained from the cultivation of algae, to a basic value (i.e. to a value higher than or equal to 10) and the subsequent addition of at least one flocculating agent. Said process allows a good collection of the algal biomass, thus obtaining a concentrated algal biomass that can be subjected to extraction of the lipids obtaining the following phases: (i) an organic phase comprising lipids which are recovered and (ii) a semi-solid phase comprising a residue of the algal biomass which is subjected to hydrolysis obtaining sugars. Furthermore, by operating according to the above process, a distinct separation of the algal biomass is obtained by flocculation, obtaining a clarified aqueous phase similar to the water used for the cultivation of the algae which can be re-used for said cultivation without being subjected to further treatments. Said process, moreover, is particularly useful in the case of a cultivation process of algae in continuous, more specifically of algae growing in salt water. Said process can also be easily reproduced and can be applied on an industrial scale.

An object of the present invention therefore relates to a process for the extraction of lipids and sugars from algal biomass, which comprises:
 producing an aqueous suspension of algal biomass;
 bringing the pH of said suspension of algal biomass to a value higher than or equal to 10, preferably ranging from 10.2 to 12, obtaining an aqueous suspension of algal biomass at basic pH;
 adding at least one anionic flocculant to said aqueous suspension of algal biomass at basic pH, obtaining a concentrated algal biomass;
 recovering said concentrated algal biomass;
 subjecting said concentrated algal biomass to extraction of the lipids obtaining:
  (i) an organic phase comprising lipids;
  (ii) a semi-solid phase comprising a residue of said algal biomass;
 subjecting said semi-solid phase (ii) to hydrolysis obtaining sugars.

For the aim of the present description and of the following claims, the definitions of the numerical ranges always comprise the extremes, unless otherwise specified.

For the aim of the present description and of the following claims, the term "comprising" also includes the terms "which essentially consists of" or "which consists of".

According to a preferred embodiment of the present invention, said process can be carried out batchwise, in semi-batch or in continuous, preferably in continuous.

According to a preferred embodiment of the present invention, said aqueous suspension of algal biomass derives from the cultivation of algae, preferably from the cultivation of microalgae.

Said microalgae can grow, alone or in a consortium with other microorganisms, in both fresh water or in water having a high salinity, for example in brackish water with a salt concentration also higher than 5 g/l. In natural ecosystems, the microalgae often coexist with other microorganisms (for example, other algae and bacteria) with which they develop interactions that increase the stability and the survival of the consortium.

For the aim of the present description and of the following claims, the term "microalgae" refers, even when not specified, to vegetal microorganisms and phototrophic and heterotrophic prokaryotes, or to consortia of microorganisms specifically cultivated which contain the same microalgae. It should be noted that for the aim of the present invention, if the above consortia are used, said consortia must prevalently contain microalgae.

Figure 2:
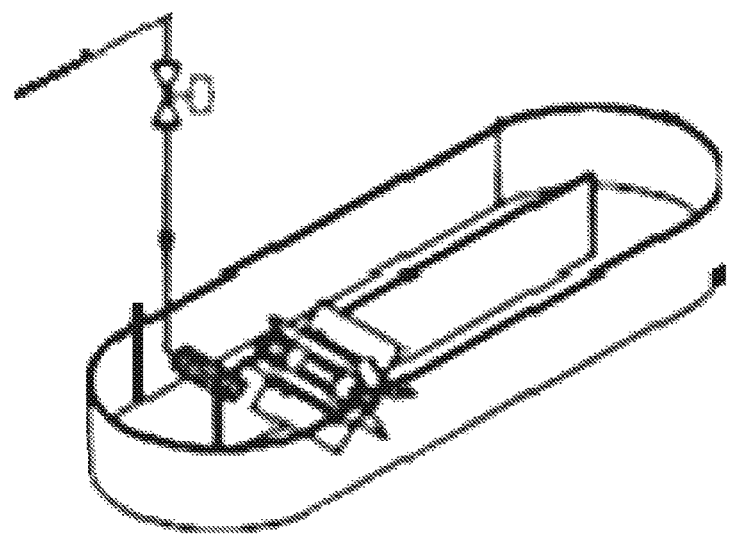
FIG. 2 shows a scheme of an open pond of the "raceway paddle wheel pond" type (Pond P-1).

For the aim of the present invention, preferably said aqueous suspension of algal biomass is obtained from the cultivation of algae in open ponds of the "raceway paddle wheel pond" type [FIG. 2 shows the scheme of an open pond of the "raceway paddle wheel pond" type (Pond P-1)] having depths greater than 0.15 m and preferably ranging from 0.2 m to 0.3 m, and active surfaces exposed to solar irradiation or by means of special lamps, in the order of a few square meters for each open pond up to 1000 $m^2$-2000 $m^2$ for each open pond in the case of open ponds of the industrial type, or from the cultivation of algae in containers, in particular, in photobioreactors having active surfaces exposed to solar irradiation or by means of special lamps, in the order of a few square meters for each photobioreactor up to 100 $m^2$-400 $m^2$ for each photobioreactor in the case of photobioreactors of the industrial type.

Specific examples of microalgae that can be advantageously used for the aim of the present invention are: *Nannochloropsys, Tetraselmis, Scenedesmus, Phaeodactylum, Chlorella, Amphipleura, Amphora, Chaetoceros, Cyclotella, Cymbella, Fragilaria, Navicula, Nitzschia, Achnantes, Dulaniella, Oscillatoria, Oocystis, Porphiridium*, or combinations thereof.

According to a preferred embodiment of the present invention, said cultivation of algae can be carried out in the presence of fresh water or of salt water coming from natural or artificial sources such as, for example, industrial processings, preferably salt water.

Preferably, said salt water can be seawater or of the brackish type, natural or artificial, also with a high salt concentration ranging, for example, from 5 g/l to 90 g/l.

An example of brackish water that can be advantageously used for the aim of the present invention is water coming from oil production fields, in particular from oil production fields in the North-African area that are situated within a context of high solar irradiation, in desert areas that cannot be used for food cultivations, and have a high co-production of water which generally has a volume several times higher than the corresponding production of oil.

If necessary, the growth of the algal biomass can be favoured by feeding nutrients based on nitrogen, phosphorous, oligo-elements, when these are not already present in the water. Solutions of organic and/or inorganic salts soluble in water are generally fed, such as, for example, ammonia salts and phosphates of alkaline or alkaline earth metals (for example, sodium, potassium, calcium, magnesium phosphates), or ammonium phosphates. Furthermore, along with water, in addition to the above nutrients, a stream of carbon dioxide ($CO_2$) is also fed, as carbon source, through special distributors deposited on the bottom of the open ponds, or suitably inserted in the growth containers (e.g., photobioreactors). The carbon dioxide contained in industrial combustion gases (refinery plants, thermoelectric plants, hydrogen generation plants, etc.), can also be used as carbon dioxide ($CO_2$).

According to a preferred embodiment of the present invention, the pH of said aqueous suspension can be brought to a value higher than or equal to 10, by the addition of at least one hydroxide of an alkaline metal, such as, for example, sodium hydroxide (NaOH), potassium hydroxide (KOH) or mixtures thereof; or of an alkaline-earth metal such as, for example, calcium hydroxide [$Ca(OH)_2$], magnesium hydroxide [$Mg(OH)_2$] or mixtures thereof; or mixtures thereof. Said hydroxide of an alkaline or alkaline-earth metal can be used as such or in aqueous solution, preferably in aqueous solution.

For the aim of the present invention, said hydroxide of an alkaline or alkaline-earth metal is added in such a quantity so as to reach the desired pH value.

According to a further preferred embodiment of the present invention, the pH of said aqueous suspension can be brought to a value higher than or equal to 10, by the complete consumption of the carbon dioxide ($CO_2$) during the growth of the algal biomass.

According to a preferred embodiment of the present invention, said anionic flocculant can be selected from high-molecular-weight anionic polymers such as, for example, polyacrylamides, polyacrylates, polymethacrylates, polycarboxylates, preferably polyacrylamides.

Said anionic polymers preferably have a molecular weight ranging from 1 MDa to 20 MDa, more preferably ranging from 2 MDa to 10 MDa.

Examples of anionic polymers that can be advantageously used for the aim of the present invention and that are commercially available are the anionic products Drylfoc® of SNF Acque Italia.

According to a preferred embodiment of the present invention, said anionic flocculant can be present in said aqueous suspension of algal biomass at basic pH in a quantity ranging from 1 ppm to 20 ppm, preferably ranging from 2 ppm to 10 ppm.

After the addition of said anionic flocculant, the concentrated algal biomass, obtained after gravitational separation, generally carried out in settlers typically used in water treatment plants (for example, lamellar pack settlers), is recovered.

The recovery of said concentrated algal biomass can be carried out according to various processes known in the art such as, for example, vacuum filtration, centrifugation, filter-presses or belt-presses, preferably filter-presses or belt-presses. Said processes allow the algal biomass to be further concentrated until a concentrated algal biomass is obtained, having a concentration of algal biomass (dry weight) ranging from 5% by weight to 30% by weight, more preferably ranging from 10% by weight to 25% by weight, with respect to the total weight of the concentrated algal biomass obtained.

For the aim of the present description and of the following claims, the term "concentration of algal biomass (dry weight)" refers to the quantity of dry algal biomass present in the concentrated algal biomass.

The water released from the recovery of the concentrated algal biomass can be largely recovered and re-used in the above process, in the production phase of algal biomass (cultivation of algae) as industrial wastewater; or, said water can be sent to a wastewater treatment plant (TAS) so that it can be subjected to finishing purification treatments before being discharged in order to reach the law specifications.

The concentrated algal biomass obtained is, on the other hand, subjected to extraction of the lipids.

According to an embodiment of the present invention, said process can comprise subjecting said concentrated algal biomass to dehydration, before extraction of the lipids, by the addition of at least one polar organic solvent selected, for example, from acetone, methanol, ethanol, ethyl acetate, methyl ethyl ketone (MEK), or mixtures thereof, preferably acetone, obtaining an aqueous phase comprising said polar organic solvent and water, and an organic phase comprising said algal biomass further concentrated.

Said dehydration is preferably carried out using a ratio between the volume of water in the aqueous suspension of concentrated algal biomass and the volume of polar organic solvent, ranging from 1:0.5 to 1:4, preferably from 1:1 to 1:2.5, at room temperature (25° C.), for a time ranging from 1 second to 10 minutes, preferably ranging from 2 seconds to 5 minutes.

Said dehydration can be carried out either with equipments of the "mixer settler" type (for example, Vortex) or with liquid-solid extractors in countercurrent. At the end of the dehydration, the aqueous phase comprising said polar organic solvent and water and the organic phase comprising said further concentrated algal biomass can be separated by means of various techniques such as, for example, filtration using drum filters, belt-presses, filter-presses, centrifuges (for example, centrifuges of the decanter type). Said dehydration offers a definite advantage from a technological point of view, as the removal of the organic solvent/water mixture and the consequent recovery of the organic solvent (for example by means of evaporation) represents a considerable energy saving with respect to removal by evaporation of the water alone contained in the starting concentrated algal biomass (the latent heat of the solvents is, in fact, equal to about a fourth of that of the water). Furthermore, the further concentration of the algal biomass allows a better extraction of the lipids, thanks to the presence of a smaller quantity of water. Said dehydration, moreover, also allows a part of the intracellular water to be removed, thus enabling the use of apolar solvents for the extraction of the lipids, as is normally the case in the vegetable oil industry. Once the solvent has been removed, for example by evaporation, the residual aqueous phase can be largely recovered and re-used in the above process, in the production phase of algal biomass (cultivation of algae) as industrial wastewater; or, said water can be sent to a wastewater treatment plant (TAS) so that it can be subjected to finishing purification treatments before being discharged in order to reach the law specifications.

According to a further embodiment of the present invention, said process can comprise subjecting said concentrated algal biomass to cell lysis, before extraction of the lipids, or after dehydration.

Said cell lysis is preferably carried out in a homogenizer, at a pressure ranging from 250 bar to 2000 bar, preferably ranging from 800 bar to 1600 bar, at room temperature (25° C.). It should be pointed out that, if a homogenizer is used, said cell lysis takes place in the order of a few milliseconds (i.e., the time for passing through the hole of said homogenizer).

According to a further embodiment of the present invention, said process can comprise subjecting said concentrated algal biomass, before or after dehydration, to cell lysis and contemporaneous extraction of lipids (Lysis and Simultaneous Extraction—LES), preferably in a homogenizer, in the presence of at least one polar organic solvent such as, for example, acetone, methanol, ethanol, ethyl acetate, methyl ethyl ketone (MEK), or mixtures thereof, preferably acetone, obtaining a mixture comprising said concentrated algal biomass, said polar organic solvent and water.

According to a further embodiment of the present invention, said process can comprise subjecting said concentrated algal biomass, before or after dehydration, to cell lysis and contemporaneous extraction of lipids (Lysis and Simultaneous Extraction—LES), preferably in a homogenizer, in the presence of at least one apolar organic solvent selected, for example, from hexane, n-octane, iso-octane, nonane, decane, isomers of xylene, toluene, benzene, chlorobenzene, dichloromethane, or mixtures thereof, refinery cuts which comprise mixtures including aliphatic and aromatic hydrocarbons, mixtures of said aliphatic and aromatic hydrocarbons, in particular mixtures known as "Light Cycle Oils" (LCO), gasoils, alkylated gasolines, or mixtures thereof, obtaining a mixture comprising said concentrated algal biomass, said apolar organic solvent and water.

The above mixture comprising said concentrated algal biomass, said polar or apolar organic solvent and water, is sent directly to separation which can be carried out by means of various techniques such as, for example, filtration using drum filters, belt-presses, filter-presses, centrifuges (for example, centrifuges of the decanter type), obtaining the above phases (i) and (ii).

Said cell lysis and contemporaneous extraction of lipids (Lysis and Simultaneous Extraction—LES) can be preferably carried out using a ratio between the volume of the aqueous suspension of concentrated algal biomass and the volume of the polar or apolar organic solvent ranging from 1:1 to 1:2, preferably 1:2, at a pressure ranging from 250 bar to 2000 bar, preferably ranging from 800 bar to 1600 bar, at room temperature (25° C.). It should be pointed out that, if a homogenizer is used, said cell lysis and contemporaneous extraction of lipids (Lysis and Simultaneous Extraction—LES) take place in the order of a few milliseconds (i.e., the time for passing through the hole of said homogenizer).

Said extraction of lipids, when carried out after cell lysis or dehydration, can be carried out by the addition of at least one apolar organic solvent selected, for example, from hexane, n-octane, iso-octane, nonane, decane, isomers of xylene, toluene, benzene, chlorobenzene, dichloromethane, or mixtures thereof, refinery cuts which comprise mixtures including aliphatic and aromatic hydrocarbons, mixtures of said aliphatic and aromatic hydrocarbons, in particular mixtures known as "Light Cycle Oils" (LCO), gasoils, alkylated gasolines, or mixtures thereof.

Alternatively, said extraction of lipids, when carried out after cell lysis or dehydration, can be carried out by the addition of at least one polar organic solvent selected, for example, from acetone, methanol, ethanol, ethyl acetate, methyl ethyl ketone (MEK), or mixtures thereof, preferably acetone.

Said extraction of lipids, when carried out after cell lysis or dehydration, can be preferably carried out using a ratio between the volume of the aqueous suspension of concentrated algal biomass and the volume of the apolar or polar organic solvent ranging from 1:1 to 1:2, preferably 1:1, at a temperature ranging from 20° C. to 100° C., preferably ranging from 50° C. to 80° C., for a time ranging from 30 minutes to 4 hours, preferably ranging from 1 hour to 3 hours.

At the end of the extraction phase of lipids, the above phases (i) and (ii) are obtained, which can be separated by gravity without requiring particular separation treatments, or they can be separated by means of processes known in the art such as, for example, filtration, centrifugation. Said phases (i) and (ii) are subsequently recovered and subjected to treatments known in the art in order to obtain the compounds of interest.

The lipid fraction present in the algal biomass deriving from the cultivation of microalgae generally comprises various classes of lipid molecules such as, for example: glycerides, for example, mono-, di-, tri-acylglycerides (composed of fatty acids and glycerol); waxes (composed of fatty acids plus alcohols and fatty acids plus sterols); hydrocarbons; free fatty acids; sterols; phospholipids, such as, for example, diacyl-phosphoglycerides, alkyl-acyl-phospholipids, alkenyl-acyl-phosphoglycerides (composed of fatty acids plus a phosphoric group), sphingophospholipids (composed of fatty acids plus a phosphoric group and nitrogenated base); glycolipids (composed of fatty acids plus carbohydrates and nitrogenated base); aminolipids (composed of fatty acids and nitrogenated base). In addition to said lipid molecules, other hydrophobic organic compounds, such as, for example, phytol and other long-chain hydrophobic alcohols, chlorophylls, carotenoids, terpenes, tocopherols, are generally present in said algal biomass.

The organic phase (i) preferably comprises, in addition to lipids, hydrophobic organic compounds different from lipids such as, for example, phytol and other alcohols.

The organic phase (i) comprising lipids and organic solvent is preferably subjected to evaporation in order to recover the organic solvent which can be re-used in the above process and the lipids extracted. After evaporation of the organic solvent, the lipids extracted can be subjected to esterification in the presence of an alcohol having from 1 to 4 carbon atoms, preferably methanol, ethanol, and of a catalyst, preferably an acid catalyst, in order to produce glycerol and alkyl esters, in particular methyl esters or ethyl esters (biodiesel).

Alternatively, after evaporation of the organic solvent, the lipids extracted can be subjected to hydrogenation/deoxygenation in the presence of hydrogen and of a catalyst with the aim of producing green diesel. Hydrogenation/deoxygenation processes are known in the art and described, for example, in European patent application EP 1,728,844.

Alternatively, said organic phase (i) comprising lipids and organic solvent can be directly subjected to esterification, or to hydrogenation/deoxygenation. In this case, the evaporation step of the organic solvent is thus avoided.

The biodiesel or green diesel which are produced as described above can be used as such or in a mixture with other fuels for motor vehicles.

The semisolid phase (ii) comprising a residue of the algal biomass, i.e. residual algal biomass soaked in the organic solvent (debris), preferably contains almost all of the carbohydrates and proteins initially present in the algal biomass.

Said semisolid phase (ii) can be subjected to hydrolysis of the polysaccharides for the production of simple fermentable sugars.

Said hydrolysis can be carried out in the presence of at least one diluted acid such as, for example, sulfuric acid, phosphoric acid, hydrochloric acid, present in a quantity ranging from 1% by weight to 5% by weight with respect to the total weight of said semi-solid phase (ii), operating, for example, at a temperature ranging from 110° C. to 160° C., for a time ranging from 1 hour to 6 hours: by operating under said conditions and at high concentrations of algal biomass in said semi-solid phase (ii), for example, at a concentration of algal biomass ranging from 20% by weight to 30% by weight with respect to the total weight of said semi-solid phase (ii), the concentrations of sugars in the hydrolyzed product obtained can be kept relatively high (e.g., concentrations >50 g/l), a fundamental characteristic for optimizing the fermentation yields in the presence of microorganisms, to which they will be subsequently sent. When operating, on the other hand, at the boiling point of the water, a complete hydrolysis can be obtained within a few hours of treatment: by operating under said conditions, the concentration of inhibitors (furfurals) deriving from the thermal degradation of the sugars is reduced to the minimum (<50 ppm), allowing the accumulation of fermentable sugars containing a quantity of growth inhibitors of the microorganisms subsequently used in fermentation which does not interfere with their growth.

Alternatively, a hydrolysis of the polysaccharides present in said semi-solid phase (ii) can be obtained, by treatment of the same with water vapour at a high temperature and pressure, optionally accompanied by a step for the sudden release of the pressure (known in the art as the "steam explosion" technique). Said treatment can be carried out without exogenous acids, as they are already present, in the reaction medium, such as, for example, acetic acid, sulfuric acid, which derive from the cell components and from the acetylated or sulfonated sugars present in the algal biomass contained in said semi-solid phase (ii). Optionally, in order to further improve the hydrolysis yields, it is in any case possible to add at least one acid such as, for example, sulfuric acid, at a low concentration, preferably at a concentration <1% by weight with respect to the total weight of said semi-solid phase (ii), in order to further improve the hydrolysis yields.

After the hydrolysis reaction, the solution of simple sugars obtained is separated from the residue (for example, by means of filtration, centrifugation, evaporation), in order to obtain a solution containing the highest possible concentration of sugars (for example, >150 g/l). In order to increase the concentration of sugars, said solution of simple sugars can be treated by means of selective membranes which, in addition to concentrating said simple sugars, can also be used for reducing the content of salts or acids dissolved in the same: the concentrated solution of sugars thus obtained can then be used for fermentations, whereas the solid residue obtained after hydrolysis, rich in protein material, can be treated separately.

The solution of simple sugars (monomeric and/or oligomeric) can be used for the fermentation of microorganisms such as, for example, yeasts, bacteria. Said solution of sugars mainly comprises glucose, mannose and xylose, other sugars such as, for example, mannitol, glucuronic acids, and is particularly rich in sugars having six carbon atoms (C6) which are easily fermentable or can be used as energy source by the microorganisms. In particular, if the production of lipids is to be increased, oleaginous yeasts are used, which are able to grow using the solution of sugars deriving from the hydrolysis of said semi-solid phase (ii). In a condition of metabolic stress (for example, when there is a lack of nitrogen), said sugars can be used as energy source for accumulating lipids (mainly triglycerides) as backup energy source: the concentration of lipids can exceed 50% by weight of the oleaginous biomass. After breakage of the cell wall of the yeasts by means of processes known in the art (for example, centrifugation and optional thermal treatment), said lipids can be quantitatively recovered by means of solvent extraction treatments (which are generally recycled), or by means of treatments which simultaneously lyse the cells of the oleaginous biomass and extract the lipids. Said lipids can be joined together with those obtained by direct extraction of the algal biomass, significantly increasing the overall yield of lipids of the whole process.

The combination of lipids obtained from the algal biomass and from the oleaginous biomass (oil) can be subjected to esterification in the presence of an alcohol having from 1 to 4 carbon atoms, preferably methanol, ethanol, and of a catalyst, preferably an acid catalyst, in order to produce glycerol and alkyl esters, in particular methyl esters or ethyl esters (biodiesel). Alternatively, said lipids can be subjected to hydrogenation/deoxygenation in the presence of hydrogen and of a catalyst in order to produce green diesel. Hydrogenation/deoxygenation processes are known in the art and described, for example, in European patent application EP 1,728,844. The biodiesel or green diesel which are produced as described above can be used as such or in a mixture with other fuels for motor vehicles.

Alternatively, the solution of sugars obtained from the hydrolysis of said semi-solid phase (ii) can be used for the fermentation of yeasts or of alcohol-producing bacteria (for example, ethanol, butanol) analogously to the case of the production of alcohols from sugars deriving from lignocellulosic biomass.

The solution of sugars obtained from the hydrolysis of said semi-solid phase (ii) can also be used for the fermentation of microorganisms, suitably selected or genetically modified, for the production of intermediates such as, for example, intermediates for the synthesis of chemical compounds, monomers for the synthesis of polymers (for example, hydroxyalkanoates), rubbers or plastic materials (for example, diols).

The solid residue obtained from the hydrolysis of said semi-solid phase (ii), characterized by a high concentration of proteins (>50%) can be used in various ways, among which, for example, as protein additive for animal nutrition (animal feeds), or as a nitrogen source and source of other essential nutrients such as, for example, phosphorous, and/or salts and/or metals for the growth and/or fermentation of microorganisms producers of biofuels.

Alternatively, said residue can be used for the production of methane as described, for example, by Briand X. et al. in "*Journal of Applied Phycology*" (1997), Vol. 9 (6), pages 511-524, or of hydrogen as described, for example, by Yang et al., in "*Journal of Chemical Technology and Biotechnology*" (2011), Vol. 86, Issue 3, pages 454-460, by means of anaerobic digestion.

Alternatively, said solid residue can be subjected to pyrolysis in order to obtain pyrolytic oil and synthesis gas ("syngas"). Alternatively, before being subjected to pyrolysis, said residue can be subjected to removal of the organic solvent which can be carried out as described hereunder. In particular, said residue, after being subjected to removal of the solvent can be subjected to high-temperature pyrolysis, for example, at a temperature ranging from 500° C. to 600° C., in order to prevalently obtain an oily phase and a gaseous phase ("syngas") and a solid residue (ashes) to be disposed of.

Alternatively, said solid residue can be subjected to anaerobic digestion by microorganisms in the absence of oxygen in order to obtain biogas.

It should be pointed out that in the case of the production of biogas, said residue must be subjected to removal of the organic solvent, which can be carried out by means of techniques known in the art such as, for example, washing with fresh solvent and subsequent drying in a thermostat-regulated oven or in industrial driers, filtration, or evaporation. After removal of the organic solvent, the residue of algal biomass obtained can be re-suspended in water in order to obtain an aqueous suspension of algal biomass to be subjected to anaerobic digestion. The organic solvent recovered can be re-used in said process.

The present invention will now be illustrated in greater detail by means of FIG. 1 provided hereunder, which indicates various embodiments of the present invention.

The aqueous suspension of algal biomass (Microalgae), obtained from the cultivation of algae, preferably microalgae, which can be conveniently carried out in open ponds (for example of the "raceway paddle wheel pond" type), in salt water, is sent to the collection phase (Separation/dewatering) carried out by the addition of at least one hydroxide of an alkaline or alkaline earth metal in order to obtain an algal biomass at basic pH (not represented in FIG. 1), addition of at least one anionic flocculant (Flocculants), recovery of the concentrated algal biomass (for example, by means of a filter-press) (Wet algal biomass).

The water separated (Water) is recovered and re-used in the above process (not represented in FIG. 1), or sent to a wastewater treatment plant (TAS) (not represented in FIG. 1), whereas the concentrated algal biomass obtained (Wet algal biomass) can be subjected to various kinds of treatment.

According to what is represented in 1, said concentrated algal biomass (Wet algal biomass) is subjected to cell lysis and contemporaneous extraction of the lipids ("Lysis and Simultaneous Extraction"—LES) (Lysis/extraction) (for example, in a homogenizer) in the presence of at least one polar organic solvent (for example, acetone), obtaining a mixture comprising concentrated algal biomass, polar organic solvent and water, which is sent to separation (S1) (for example, by means of a centrifuge) obtaining the above phase (i) [Extract (organic phase)] and phase (ii) (Debris). Said phase (i) [Extract (organic phase)] is subjected to further separation (S2) (for example, by means of evaporation), obtaining polar organic solvent which is re-used in the above process and will be used either in the extraction phase of lipids (Extraction of lipids) or in the cell lysis and contemporaneous extraction ("Lysis and Simultaneous Extraction"—LES) phase (Lysis/extraction) of the lipids (Lipid Extract), which are subjected to the treatments described above for obtaining biodiesel or green diesel (not indicated in FIG. 1). It should be pointed out that, if particular known mixtures (already indicated above) such as "Light Cycle Oil" (LCO), gasoils, alkylated gasolines, or mixtures thereof, are used as extraction solvent of the lipids, said lipids (Lipid Extract) can be sent directly to refinery processes for the production of biodiesel or green diesel without being subjected to said further separation (S2).

Said phase (ii) (Debris) is subjected to hydrolysis (Breakage of polysaccharides) (for example, in the presence of diluted acids), obtaining a solution of sugars and a solid residue which are sent to separation (S5) (for example, by means of filtration or centrifugation), obtaining a residue prevalently comprising proteins (Protein residue) which can be used in zootechnics (Animal feeds) or which can be sent for treatments for producing energy (Energy Upgrading) such as, for example, high-temperature pyrolysis for obtaining synthesis gas (Syngas) and pyrolytic oil (Oil), and a solution of sugars (Simple sugars) which is sent to fermentation (Fermentation A) in the presence, for example, of oleaginous yeasts (Yeasts), obtaining lipids, which are added to the concentrated algal biomass obtained from the separation/dewatering phase [Recycling (lipids)], or to fermentation (Fermentation B) in the presence of microorganisms capable of producing ethanol (Ethanol).

According to what is represented in 2, said concentrated algal biomass (Wet algal biomass) is subjected to cell lysis (Lysis) (for example, by means of homogenization, at high pressure) and subsequent extraction of the lipids carried out as described above (Extraction of lipids), obtaining the above phase (i) (Lipid Extract) and phase (ii) (Debris), which are treated as described above.

According to what is represented in 3, said concentrated algal biomass (Wet algal biomass) is subjected to dehydration (Dehydration), for example, by the addition of a polar solvent (Polar Solvent) obtaining an aqueous phase comprising said polar organic solvent and water and a further concentrated algal biomass. Said further concentrated algal biomass is sent to separation (S3) (for example, by means of a filter-press), obtaining an aqueous phase comprising the polar organic solvent and water. Said aqueous phase is sent to separation (S4) (for example, by means of evaporation), obtaining water which is sent to further treatment (Water Treatment) and polar organic solvent (Polar Solvent) which is re-used in the dehydration phase, and an organic phase comprising concentrated algal biomass which is sent to extraction of the lipids carried out as described above (Extraction of lipids), obtaining the above phase (i) (Lipid Extract) and phase (ii) (Debris), which are treated as described above.

Some illustrative and non-limiting examples are provided for a better understanding of the present invention and for its embodiment.

EXAMPLE 1

Preparation of the Algal Biomass

In the following examples, the algal strain *Nannochloropsis* sp., of internal collection, which normally grows in seawater, was used. The cultivation process adopted is described hereunder.

The inoculum to be introduced into the open pond growth indicated hereunder, was prepared as follows:
- a sample of monoalgal culture previously preserved at −85° C. in a 10% glycerine solution, was defrosted leaving it at room temperature, and was then subjected to centrifugation to remove the supernatant, obtaining a cell paste;
- the cell paste thus obtained was inoculated into three 250 ml flasks containing 50 ml of solution comprising nutrients, obtaining an algal culture;
- said algal culture was grown in an illuminated climatic chamber at a constant temperature of 30° C., in the presence of carbon dioxide ($CO_2$) at 0.5% in air;
- after about a week, the flask reached a concentration of 0.3 g/l, this culture was used as inoculum for three 1 liter flasks containing 500 ml of solution comprising nutrients and placed in the climatic chamber;
- after 2 days the culture had a concentration of 0.5 g/l and this culture was used as mentioned above, as inoculum for a laboratory open pond growth having a volume of 35 liters.

The inoculum, prepared as described above, was grown in the culture medium F/2, described in literature for the cultivation of microalgae. The growth conditions used were the following:
Water: artificial seawater (salinity 33 g/l);
$NaNO_3$: 75 mg/l;
$NaH_2PO_4.H_2O$: 5 mg/l;
$NaSiO_3.9H_2O$: 30 mg/l;
$Na_2EDTA$: 4.36 mg/l;
$COCl_2.6H_2O$: 0.01 mg/l;
$CuSO_4.5H_2O$: 0.01 mg/l;
$FeCl_3.6H_2O$: 3.15 mg/l;
$MnCl_2.4H_2O$: 0.18 mg/l;
$Na_2MoO_4.2H_2O$: 0.006 mg/l;
$ZnSO_4.7H_2O$: 0.022 mg/l;
Thiamine HCL: 0.1 mg/l;
Biotin: 0.0005 mg/l;
B12: 0.0005 mg/l;
Operating pH: 7.8.
Open pond growth inoculum: 10% by volume of the above culture in F/2 medium.

The growth open pond was illuminated from the outside by means of 17500 Lux tungsten lamps and was maintained at 28° C. by means of thermostat-regulated water circulation. Said open pond was also fed with a mixture of air and carbon dioxide ($CO_2$) at 10% in air, at a flow-rate of 200 liters/hour, under a pH control (pH set point 7.0).

The culture thus prepared had an algal concentration equal to 0.5 g/l and was used for inoculating open ponds of the "raceway paddle wheel pond" type, positioned outside, having a surface equal to 2.5 $m^2$, a depth equal to 0.15 cm and a volume equal to 375 l. The open ponds of the "raceway paddle wheel pond" type were equipped with a circular blade for keeping the microalgal culture under constant stirring (rate of 30 cm/s) and had a longitudinal division so as to create, by the stirring of the blade, a continuous circular flow. Said open ponds were equipped with sensors for monitoring the temperature, the pH and the concentration of dissolved oxygen.

The carbon source consisted of gaseous carbon dioxide ($CO_2$), which was introduced directly into the reactors and regulated by measuring the pH. As already indicated above, FIG. 2 shows the scheme of an open pond of the "raceway paddle wheel pond" type.

Once the cultures grown in the open ponds had also reached a concentration equal to 0.4 g/l-0.5 g/l, said cultures were transferred to open ponds of the "raceway paddle wheel pond" type, positioned outside, having a surface equal to 50 $m^2$, a depth equal to 20 cm and a volume equal to 10 $m^3$, and put into production.

Said production consisted of the daily collection of 40% of the culture, which was subjected to the collection phase (separation/dewatering), whereas fresh culture medium consisting in the medium F/2, described above, in seawater, was renewed in the open ponds. The carbon dioxide source ($CO_2$) for these open ponds was taken from the discharge gas emitted from a partial oxidation plant of methane for the production of hydrogen for oil refinery processes.

The production of the open ponds was determined by multiplying the value of the concentration of algal biomass (dry weight) by the volume of culture collected, whereas the daily concentration of algal biomass expressed in grams/l was determined by means of dry weight measurements which were carried out as follows:
- a known volume of culture (e.g., a liter) was filtered on a Whatman filter with a porosity of 0.42 microns so that the algal biomass and the inert solids in suspension remained adhered to the filter;
- the filter was dried at 105° C., for 3 hours, so as to remove the imbibition water;
- the weight of the filter dried at 105° C. provided a quantity of algal biomass and of inert solids present in the culture;
- the filter was then calcined at 550° C. to eliminate the part of algal biomass and to determine the inert solids present in the algal culture;
- the difference in weight between the filter dried at 105° C. and the same filter calcined at 550° C. provided the quantity of algal biomass contained in a liter of culture and the value obtained was indicated as concentration of the culture (due only to the weight of the organic mass coming from the microalgae) and is the reference value for calculating the areal productivity and for calculating the lipid, protein and sugar content of the culture.

Typical values measured of organic content (volatile solids) and of inert solids content, are the following:
- volatile solids from 55% to 70% of the total weight of algal biomass plus inert solids;
- inert solids from 30% to 45% of the total weight of algal biomass plus inert solids.

The productivity was also calculated, operating as follows:
- the productivity, expressed in grams (dry weight), of algal biomass collected daily, was obtained by multiplying the concentration value of the culture (determined as described above) by the liters removed daily from each open pond;
- the definite areal productivity is the productivity calculated as described above, referring to the effective surface unit of each open pond, this datum was obtained by dividing the value of said productivity by the square meters of effective surface of each open pond which, in this case, were equal to 50 m²;
- the daily areal productivity is therefore expressed in grams produced (dry weight) per square meter per day.

Figure 3:
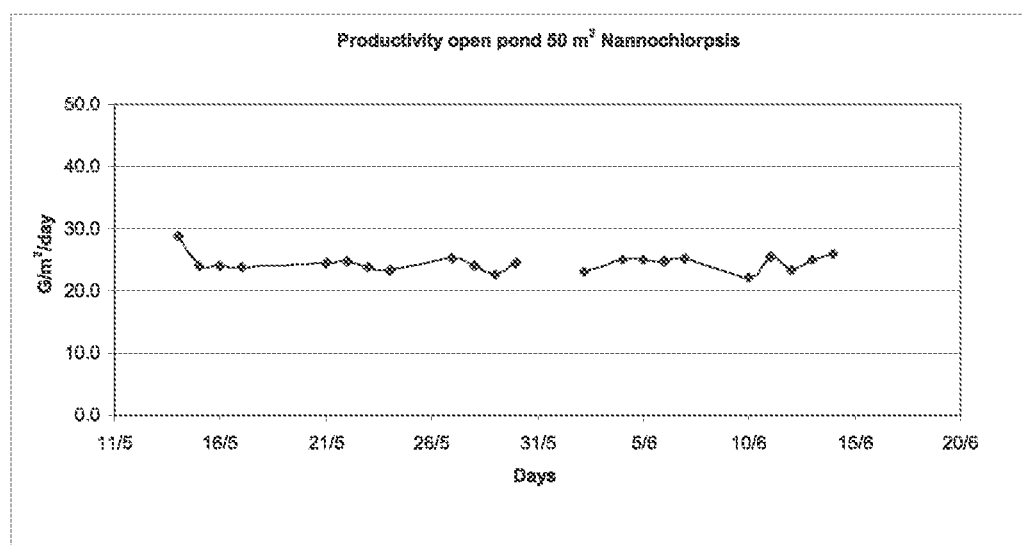
FIG. 3 shows a graph with the daily areal productivities during the algal production The lipids thus obtained can be advantageously used in the production of biodiesel or green diesel which can be used as such, or in a mixture with other fuels for motor vehicles.

FIG. 3 shows a graph with the daily areal productivities during the algal production referring to an open pond (in ordinate are reported the g/m²/day, in abscissa are reported the days).

The aqueous suspension of algal biomass coming from the open ponds was mixed with an aqueous solution of calcium hydroxide [Ca(OH)$_2$] at 5%, by means of a static mixer, thus bringing the pH from 7.5 to 10.5. The aqueous suspension of algal biomass at pH 10.5 was then mixed, by means of a second static mixer, with an aqueous solution of anionic flocculant (Dryfloc® 976), previously prepared at a concentration of 1 g/l, thus obtaining a concentration of flocculant in the aqueous suspension of algal biomass equal to 4 ppm.

The aqueous suspension of algal biomass thus treated was introduced into a lamellar pack settler (Accadueo Impianti srl) having a capacity equal to 15 m³. After 30 minutes, the concentrated algal biomass obtained, was removed from the bottom of the settler: said concentrated algal biomass had a concentration of algal biomass (dry weight) equal to about 40 g/l.

Various samples of said concentrated algal biomass were pushed, by means of a pump, through the filters of a filter-press, operating at a pressure ranging from 2 atm to 4 atm. The algal biomass remaining on the filters was subsequently removed obtaining a concentrated algal biomass having a concentration of algal biomass (dry weight) ranging from 10% by weight to 20% by weight, with respect to the total weight of said concentrated algal biomass, depending on the operating pressure. The clarified water, on the other hand, which passed through the filter-press was recycled to the open ponds.

The concentrated algal biomass thus obtained was characterized for determining the percentage quantity of lipids, proteins and carbohydrates: Table 1 below indicates the average percentage values obtained and the analytical methods used for their determination.

TABLE 1

| Substance | Analytical method | Quantity (% w/dry w) |
| --- | --- | --- |
| Proteins | Bradford, Bio-rad Protein "Assay Analytical Biochemistry" (1976) Vol. 72, pages 248 | 56 ± 3 |
| Lipids | Bligh and Dyer, "Journal of Biochemistry and Physiology" (1959), Vol. 37, pages 911-917 | 15 ± 2 |
| Carbohydrates | Trevelyan and Harrison, "Archives of Biochemistry and Biophysic" (1952), Vol. 39(2), pages 419-439 | 29 ± 2 |

EXAMPLE 2

Lysis with a Homogenizer and Subsequent Lipid Extraction

A sample of wet concentrated algal biomass (800 g) produced as described in Example 1, having a concentration of algal biomass (dry weight) equal to 12% by weight with respect to the total weight of said wet concentrated algal biomass, of which 44% of inert solids and 56% of volatile solids (organic part) and having a lipid content of 29% by weight with respect to the total weight of the volatile solids, determined with the method indicated in Table 1, was subjected to homogenization (homogenizer GEA 3006L of Niro Soavi), operating at 1,500 bar, at room temperature (25° C.)

500 ml of the algal biomass obtained after homogenization were incubated in a two-liter flask, for hours, at 63° C., with 1 l of acetone. After bland centrifugation, the supernatant was recovered (1370 ml) comprising water, acetone and lipids.

The solid residue comprising the algal biomass was washed twice with 200 ml of acetone: the washings were recovered and added to the supernatant (total volume of supernatant 1770 ml), and the remaining solid residue was dried in the air obtaining a residue of dry algal biomass.

Dichloromethane was added to the supernatant in a ratio of 3:1 with the supernatant, obtaining a mixture. Said mixture was subjected to stirring so that the lipids completely dissolved in the dichloromethane obtained two immiscible phases. Said immiscible phases consisting of the mixture water/acetone and dichloromethane/lipids were separated by means of a separating funnel. The dichloromethane was removed from the dichloromethane/lipids phase by evaporation, the quantity of lipids remaining was then determined by weighing.

19 g of lipids were obtained, equal to 26.8% by weight with respect to the volatile solids present in the starting wet concentrated algal biomass. This value indicates that, with the process object of the present invention, which can be adopted on an industrial scale, 92.4% of the total lipids contained in the starting wet concentrated algal biomass can be extracted, which were determined according to the analytical method indicated in Table 1.

EXAMPLE 3

Dehydration with a Polar Solvent and Subsequent Lipid Extraction 485 g of acetone were added to a sample of wet concentrated algal biomass (310 g) produced as described in Example 1, having a concentration of algal biomass (dry weight) equal to 21.67% by weight with respect to the total weight of said wet concentrated algal biomass, of which 34.5% of inert solids and 65.5% of volatile solids (organic part) and having a lipid content of 29% by weight with respect to the total weight of the volatile solids, determined with the method indicated in Table 1, for a water:acetone ratio equal to 1:2.

After mixing in a Vortex for 4 seconds, the mixture obtained was centrifuged at 2,500 rpm, for 4 seconds. 120 g of acetone were added to the residue obtained, for a ratio initial water:acetone equal to 1:0.5, and the whole mixture was mixed again in a Vortex for 4 seconds, with centrifugation at 2,500 rpm, for 4 seconds.

The wet algal biomass (267 g) recovered proved to have the following composition: 21.86% by weight with respect to the total weight of said wet concentrated algal biomass of algal biomass (dry weight), of which 33.28% of inert solids and 66.72% of volatile solids (organic part) and having a lipid content of 29% by weight with respect to the total weight of the volatile solids, determined with the method indicated in Table 1. The liquid phase, which corresponds to 78.14% of said wet algal biomass, consisted for 80% of acetone and only 20% of water.

A sample of the above wet algal biomass (6.8 g) was subjected to lipid extraction using acetone as polar solvent: for this aim, the wet algal biomass was incubated for two hours, in a two-necked 100 ml flask, at a temperature of 65° C.÷70° C., with 20 ml of acetone (ratio wet algal biomass: acetone equal to 1:3), obtaining a supernatant (26 ml) consisting of water/acetone/lipids and a residual algal biomass (debris) which were separated by filtration.

The solid residue comprising the residual algal biomass (debris) was washed twice with 200 ml of acetone: the washings were recovered and added to the supernatant (total volume supernatant 205 ml), and the remaining solid residue was dried in the air obtaining a residue of dry algal biomass.

The determination of the lipids was carried out as described in Example 2.

281 g of lipids were obtained, equal to 27.94% by weight with respect to the volatile solids present in the starting wet concentrated algal biomass. This value indicates that, with the process object of the present invention, which can be adopted on an industrial scale, 96.3% of the total lipids contained in the starting wet concentrated algal biomass, which were determined according to the analytical method indicated in Table 1, can be extracted.

EXAMPLE 4

Lysis and Simultaneous Solvent Extraction ("Lysis and Simultaneous Extraction"—LES)

160 g of acetone were added to a sample of concentrated algal biomass (100 g) produced as described in Example 1, having a concentration of algal biomass (dry weight) equal to 20% by weight with respect to the total weight of said wet concentrated algal biomass, of which 35% of inert solids and 65% of volatile solids (organic part) and having a lipid content of 14.16% by weight with respect to the total weight of the volatile solids, determined with the method indicated in Table 1, for a water:acetone ratio of 1:2, and the whole mixture was subjected to homogenization (homogenizer GEA 3006L of Niro Soavi), operating at 1,500 bar, at room temperature (25° C.)

The wet algal biomass obtained after homogenization was centrifuged at 2500 rpm and the supernatant (165 ml) comprising water, acetone and lipids, was recovered.

The solid residue comprising the dry algal biomass was washed twice with 200 ml of acetone: the washings were recovered and added to the supernatant (total volume of supernatant 565 ml), and the remaining solid residue was dried in the air obtaining a residue of dry algal biomass.

The determination of the lipids was carried out as described in Example 2.

2.45 g of lipids equal to 12.27% by weight with respect to the volatile solids present in the starting wet concentrated algal biomass, were obtained. This value indicates that, with the process of the present invention, which can be adopted on an industrial scale, 86.65% of the total lipids contained in the starting wet concentrated algal biomass, which were determined according to the analytical method indicated in Table 1, can be extracted.

EXAMPLE 5

Hydrolysis and Extraction of Sugars

A sample (10 g) consisting of a residue of dry algal biomass (debris) obtained downstream of the lipid extraction described in Example 2, was subjected to acid hydrolysis in order to make the complex sugars present in the starting dry algal biomass (debris), simple (monomers).

For this aim, 20 ml of water were added to said sample together with the quantity of sulfuric acid necessary for obtaining a pH of the solution equal to 1, obtaining a suspension of algal biomass.

The suspension thus obtained was subjected to stirring for 5 minutes, subsequently brought, always under stirring, to 141° C., by means of a thermostatic batch, and left at this temperature for 5 hours.

The resulting simple sugars downstream of the hydrolysis, were dissolved in the aqueous phase of the suspension. The aqueous phase, rich in simple sugars, was then separated from the cell "debris" by means of centrifugation, at 2500 rpm.

For the determination of the sugars present in the isolated aqueous phase, the method cited in the publication of Trevelyan and Harrison, "*Archives of Biochemistry and Biophysic*" (1952), Vol. 39(2). pages 419-439, was adopted.

The quantity of simple sugars obtained proved to be equal to about 50% of the total sugars which proved to be equal to 12% in the starting algal biomass (debris) which were determined with the same method indicated above and also specified in Table 1.

The invention claimed is:

1. A process for extracting lipids and sugars from algal biomass, the process comprising:
adjusting the pH of an aqueous suspension of algal biomass to a value of 10.2 to 12 by adding at least one hydroxide of an alkaline metal, or at least one hydroxide of an alkaline-earth metal, or a mixture thereof; or as the algae consumes carbon dioxide ($CO_2$) during the growth of the algal biomass, thereby obtaining an aqueous suspension of algal biomass at a basic pH;

adding at least one anionic flocculant to said aqueous suspension of algal biomass at the basic pH, thereby obtaining a concentrated algal biomass;

recovering said concentrated algal biomass leaving a clarified aqueous phase;

subjecting said concentrated algal biomass to lipid extraction, thereby obtaining:
(i) an organic phase comprising lipids; and
(ii) a semi-solid phase comprising a residue of said algal biomass;

subjecting said semi-solid phase (ii) to hydrolysis, thereby obtaining the sugars; and recycling the clarified aqueous phase to cultivation of algae without further treatment.

2. The process according to claim 1, which is carried out in a batch, semi-batch or continuous process.

3. The process according to claim 1, wherein said aqueous suspension of algal biomass derives from the cultivation of algae.

4. The process according to claim 3, wherein said cultivation of algae is carried out in the presence of fresh water or salt water coming from natural or artificial sources.

5. The process according to claim 1, wherein the pH of said aqueous suspension is adjusted by adding at least one hydroxide of an alkaline metal, or at least one hydroxide of an alkaline-earth metal, or a mixture thereof.

6. The process according to claim 1, wherein the pH of said aqueous suspension changes as the algae consumes carbon dioxide ($CO_2$) during the growth of the algal biomass.

7. The process according to claim 1, wherein said anionic flocculant is a high-molecular-weight anionic polymer.

8. The process according to claim 7, wherein said anionic polymer has a molecular weight ranging from 1 MDa to 20 MDa.

9. The process according to claim 1, wherein said anionic flocculant is present in said aqueous suspension of algal biomass at the basic pH in a quantity ranging from 1 ppm to 20 ppm.

10. The process according to claim 1, further comprising subjecting said concentrated algal biomass to dehydration, before extraction of the lipids, by adding at least one polar organic solvent selected from the group consisting of acetone, methanol, ethanol, ethyl acetate, methyl ethyl ketone (MEK), or a mixture thereof, thereby obtaining an aqueous phase comprising said polar organic solvent and water, and an organic phase comprising said algal biomass, further concentrated.

11. The process according to claim 10, further comprising:
subjecting said concentrated algal biomass to cell lysis, before extraction of the lipids, or after dehydration,
wherein said cell lysis is carried out at a pressure ranging from 250 bar to 2000 bar and at room temperature of 25° C.

12. The process according to claim 11, wherein said extraction of lipids, when carried out after cell lysis or dehydration, is carried out by adding at least one apolar organic solvent selected from the group consisting of hexane, n-octane, iso-octane, nonane, decane, an isomer of xylene, toluene, benzene, chlorobenzene, dichloromethane, or a mixture thereof, a refinery cut which comprises a mixture of aliphatic and aromatic hydrocarbons.

13. The process according to claim 12, wherein said extraction of lipids, when carried out after cell lysis or dehydration, is carried out at a volume ratio of the aqueous suspension of concentrated algal biomass to the apolar organic solvent of from 1:1 to 1:2, at a temperature ranging from 20° C. to 100° C., for a time ranging from 30 minutes to 4 hours.

14. The process according to claim 11, wherein said extraction of lipids, when carried out after cell lysis or dehydration, is carried out by adding at least one polar organic solvent selected from the group consisting of acetone, methanol, ethanol, ethyl acetate, methyl ethyl ketone (MEK), or a mixture thereof.

15. The process according to claim 14, wherein said extraction of lipids, when carried out after cell lysis or dehydration, is carried out at a volume ratio of the aqueous suspension of concentrated algal biomass to the polar organic solvent of from 1:1 to 1:2 at a temperature ranging from 20° C. to 100° C. for a time ranging from 30 minutes to 4 hours.

16. The process according to claim 10, further comprising:
subjecting said concentrated algal biomass, before or after dehydration, to cell lysis and contemporaneous extraction of lipids in the presence of at least one polar organic solvent, thereby obtaining a mixture comprising said concentrated algal biomass, said polar organic solvent and water.

17. The process according to claim 16, wherein said cell lysis and contemporaneous extraction of lipids is carried out at a volume ratio of the aqueous suspension of concentrated algal biomass to the polar organic solvent of from 1:1 to 1:2 at a pressure ranging from 250 bar to 2000 bar and at room temperature of 25° C.

18. The process according to claim 10, further comprising:
subjecting said concentrated algal biomass, before or after dehydration, to cell lysis and contemporaneous extraction of lipids in the presence of at least one apolar organic solvent selected from the group consisting of hexane, n-octane, iso-octane, nonane, decane, an isomer of xylene, toluene, benzene, chlorobenzene, dichloromethane, or a mixture thereof, a refinery cut which comprises a mixture of aliphatic and aromatic hydrocarbons, thereby obtaining a mixture comprising said concentrated algal biomass, said apolar organic solvent and water.

19. The process according to claim 18, wherein said cell lysis and contemporaneous extraction of lipids is carried out at a volume ratio of the aqueous suspension of concentrated algal biomass to the apolar organic solvent of from 1:1 to 1:2 at a pressure ranging from 250 bar to 2000 bar and at room temperature of 25° C.

20. The process according to claim 1, wherein said hydrolysis is carried out:
in the presence of at least one diluted acid in an amount ranging from 1% by weight to 5% by weight with respect to a total weight of said semi-solid phase (ii), at a temperature ranging from 110° C. to 160° C., for a time ranging from 1 hour to 6 hours; or at the boiling point of water; and
by treating the semi-solid phase (ii) with water vapour at a temperature and pressure, optionally accompanied by a sudden release of the pressure, optionally in the presence of an acid in an amount of less than 1% by weight with respect to the total weight of said semi-solid phase (ii).

\* \* \* \* \*